United States Patent
Wu et al.

(10) Patent No.: US 9,070,181 B2
(45) Date of Patent: Jun. 30, 2015

(54) SYSTEM AND METHOD FOR EXTRACTING FEATURES OF INTEREST FROM AN IMAGE

(75) Inventors: Xiaoye Wu, Rexford, NY (US); David Allen Langan, Clifton Park, NY (US); James Vradenburg Miller, Clifton Park, NY (US); Yogisha Mallya, Bangalore (IN); Srikanth Suryanarayanan, Bangalore (IN)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 2320 days.

(21) Appl. No.: 11/962,507

(22) Filed: Dec. 21, 2007

(65) Prior Publication Data

US 2009/0161939 A1 Jun. 25, 2009

(51) Int. Cl.
  *G06K 9/00* (2006.01)
  *G06T 7/00* (2006.01)
  *A61B 6/00* (2006.01)

(52) U.S. Cl.
  CPC ............... *G06T 7/0012* (2013.01); *A61B 6/482* (2013.01); *G06T 7/0081* (2013.01); *G06T 2207/10116* (2013.01); *G06T 2207/10152* (2013.01); *G06T 2207/30016* (2013.01); *G06T 2207/30101* (2013.01)

(58) Field of Classification Search
  None
  See application file for complete search history.

(56) References Cited

U.S. PATENT DOCUMENTS

| | | | | |
|---|---|---|---|---|
| 4,445,226 A | * | 4/1984 | Brody | 378/98.9 |
| 4,482,918 A | * | 11/1984 | Keyes et al. | 378/98.11 |
| 4,611,341 A | * | 9/1986 | Brody | 378/98.11 |
| 4,780,897 A | * | 10/1988 | McDaniel et al. | 378/62 |
| 5,244,469 A | * | 9/1993 | Shimoyama et al. | 8/438 |
| 6,891,918 B2 | * | 5/2005 | Drummond et al. | 378/5 |
| 6,898,263 B2 | * | 5/2005 | Avinash et al. | 378/4 |
| 6,901,281 B2 | * | 5/2005 | Bjørnerud et al. | 600/420 |
| 7,020,314 B1 | * | 3/2006 | Suri et al. | 382/130 |
| 7,123,760 B2 | * | 10/2006 | Mullick et al. | 382/131 |
| 7,298,812 B2 | * | 11/2007 | Tkaczyk et al. | 378/5 |
| 7,372,934 B2 | * | 5/2008 | De Man et al. | 378/4 |
| 7,599,541 B2 | * | 10/2009 | Hayashida | 382/132 |
| 7,668,361 B2 | * | 2/2010 | Spies | 382/132 |
| 7,689,019 B2 | * | 3/2010 | Boese et al. | 382/128 |
| 7,778,454 B2 | * | 8/2010 | Grasruck et al. | 382/128 |

(Continued)

FOREIGN PATENT DOCUMENTS

| | | | |
|---|---|---|---|
| JP | 62290443 A | 12/1987 | |
| JP | 0263439 A | 3/1990 | |

(Continued)

OTHER PUBLICATIONS

Vinhais et al. "Lung Parenchyma Segmentation from CT Images Based on Material Decomposition" Springer Verlag Berlin Heidelberg 2006; ICIAR 2006, LNCS 4142, pp. 624-635.*

(Continued)

*Primary Examiner* — Chan Park
*Assistant Examiner* — Mia M Thomas
(74) *Attorney, Agent, or Firm* — Fletcher Yoder, P.C.

(57) ABSTRACT

A technique is provided for extracting one or more features of interest from one or more projection images. The technique includes accessing projection images comprising at least one feature of interest enhanced by a contrast agent, generating a contrast agent null image based on the projection images, generating a bone mask based on the contrast agent null image, and generating a bone extracted image based on the bone mask.

22 Claims, 5 Drawing Sheets

(56) References Cited

U.S. PATENT DOCUMENTS

| | | | |
|---|---|---|---|
| 7,920,735 B2* | 4/2011 | Krauss et al. | 382/132 |
| 8,103,067 B2* | 1/2012 | Boese et al. | 382/128 |
| 8,509,384 B2* | 8/2013 | Spahn | 378/98.12 |
| 2001/0031038 A1* | 10/2001 | Suzuki | 378/182 |
| 2002/0025063 A1* | 2/2002 | Jiang et al. | 382/132 |
| 2002/0076090 A1* | 6/2002 | Lee et al. | 382/128 |
| 2002/0181755 A1* | 12/2002 | Lee et al. | 382/132 |
| 2003/0013953 A1* | 1/2003 | Mistretta | 600/425 |
| 2003/0152258 A1* | 8/2003 | Jabri et al. | 382/132 |
| 2003/0194120 A1* | 10/2003 | Unger et al. | 382/132 |
| 2004/0101104 A1* | 5/2004 | Avinash et al. | 378/98.12 |
| 2005/0015006 A1* | 1/2005 | Mitschke et al. | 600/431 |
| 2005/0111719 A1* | 5/2005 | Pescatore et al. | 382/132 |
| 2005/0111722 A1* | 5/2005 | Gerwin | 382/132 |
| 2005/0180541 A1* | 8/2005 | Avinash et al. | 378/5 |
| 2005/0228272 A1* | 10/2005 | Yu | 600/425 |
| 2006/0188139 A1* | 8/2006 | Khamene et al. | 382/130 |
| 2006/0291711 A1* | 12/2006 | Jabri et al. | 382/132 |
| 2007/0167716 A1* | 7/2007 | Kinahan et al. | 600/407 |
| 2007/0195932 A1* | 8/2007 | Nakaura et al. | 378/98.12 |
| 2010/0226537 A1* | 9/2010 | Villain et al. | 382/103 |
| 2010/0278407 A1* | 11/2010 | Dzyubak et al. | 382/131 |

FOREIGN PATENT DOCUMENTS

| | | |
|---|---|---|
| JP | 04208138 A | 7/1992 |
| JP | 11318883 A | 11/1999 |
| JP | 2004174262 A | 6/2004 |
| JP | 2007135699 A | 6/2007 |
| JP | 2007268273 A | 10/2007 |

OTHER PUBLICATIONS

Johnson et al. "Material differentiation by dual energy CT: initial experience" Eur Radiol (2007) Dec. 7, 2006, pp. 1510-1517.*

General Electric Medcyclopaedia—Projection X-ray Images, pp. 1-3.*

Netherlands Search Report dated Oct. 1, 2010 and Written Opinion.

Johnson et al., "Material Differentiation by Dual Energy CT: Initial Experience", European Journal of Radiology, vol. 17, pp. 1510-1517, Jun. 2007.

Venema et al., "CT Angiography of the Circle of Willis and Intracranial Internal Carotid Arteries: Maximum Intensity Projection With Matched Mask Bone Elimination—Feasibility Study", Radiology, vol. 218, pp. 893-898, 2001.

JP Office Action mailed Feb. 12, 2014, Application 2008-321817, pp. 1-3.

* cited by examiner

SYSTEM AND METHOD FOR EXTRACTING FEATURES OF INTEREST FROM AN IMAGE

BACKGROUND

The invention relates generally to the field of medical imaging and in particular to a technique of extracting one or more features of interest from a radiographic image.

In the field of medical care, a wide variety of radiographic imaging modalities may be used for imaging patients. Such modalities include, for example, conventional projection X-ray systems, computed tomography (CT) systems, dual energy CT systems, tomosynthesis systems, C-arm systems, and so forth. These imaging modalities acquire projection images of an anatomy of interest within the patient. The projection images, upon reconstruction, reveal the internal structures (e.g., bones, blood vessels, soft tissues, and so forth) of the imaged anatomy due to the different densities of these structures, and resulting differences in the attenuation or absorption of incident X-rays. However, some structures are not clearly visible in the reconstructed image due to their low radio-opacity. Typically, a contrast agent may be employed during medical examinations to highlight specific structures within the imaged anatomy. Thus, vasculature and other structures may be imaged by administration of contrast agent (e.g., iodine) prior to imaging. The relative attenuation may be referred to in terms of "Hounsfield units". Contrast agents serve temporarily to increase these values in tissues in which the contrast agents propagate.

In many applications, it is useful to extract the contrast agent enhanced structures, particularly blood vessels, for evaluation by qualified professionals. This can be done by automated or semi-automated algorithms that perform "segmentation", or the identification of pixels or voxels in image data that correspond to locations of each tissue type. However, in the presence of contrast agents, the elevated Hounsfield units value in such tissues makes the blood vessel appear similar to bone, complicating the distinction between these. Thus, in the automatic vessel segmentation process, it becomes very difficult to differentiate bone from blood vessels, especially when the two come very close to each other in Hounsfield unit values due to the contrast agent.

Digital subtraction angiography (DSA) is one technique commonly used to automatically extract (identify and segment) contrast agent enhanced vessels. In such techniques, a mask image acquisition is performed prior to administering contrast agents to capture bone and soft tissue components in a non-contrast enhanced image. A second image acquisition is then performed after the administration of contrast agent, in which bone, soft tissue, and contrast enhanced vessels will be visible, with the vessel visibility being greatly enhanced over that of the previous image. The contrast enhanced blood vessel is then extracted by comparing the first and second images. However, there is a significant time lag between these two acquisitions, and a proper comparison requires fairly closely aligned or alignable images. DSA is therefore typically limited in application to portions of the patient's anatomy that can remain motionless for many seconds.

Alternatively, material decomposition techniques may be employed to extract the contrast agent enhanced structure directly from dual energy scan data. Dual energy systems are currently being developed that can make two or more images based upon application of different X-ray energy levels. However, material decomposition techniques do not provide robust results if the imaged object contains more than one material other than the contrast as the technique targets material having fixed chemical composition. For example, bones and contrast agent enhanced vessels may be isolated directly using material decomposition. However, the bones may be of different chemical compositions in a human body. Thus, material decomposition that works on a given target chemical composition will fail to account for all types of bones. The use of present techniques has simply not provided the ability to distinguish between all three types of tissues, bone, soft tissue, and contrast-enhanced vessel tissue.

It is therefore desirable to provide an efficient technique for extracting contrast-enhanced structures (e.g., blood vessels) from a radiographic image with improved accuracy and reliability.

BRIEF DESCRIPTION

Briefly, in accordance with one aspect of the technique, a method is provided for extracting one or more features of interest from one or more projection images. The method provides for accessing projection images comprising at least one feature of interest enhanced by a contrast agent, generating a contrast agent null image based on the projection images, generating a bone mask based on the contrast agent null image, and generating a bone extracted image based on the bone mask. Systems and computer programs that afford such functionality may be provided by the present technique.

In accordance with another aspect of the technique, a method is provided for extracting one or more features of interest from projection images. The method provides for acquiring the projection images of an anatomy of interest by exposing the anatomy of interest to at least two different X-ray energy levels. The anatomy comprises at least one feature of interest administered with a contrast agent. The method further provides for generating a contrast agent null image based on the projection images via a material decomposition technique, generating a binary bone mask from the contrast agent null image via an automated bone segmentation technique, and generating a bone extracted image by comparing an image representation of the anatomy of interest and the binary bone mask. Here again, systems and computer programs affording such functionality may be provided by the present technique.

In accordance with a further aspect of the present technique, an image analysis system is provided. The image analysis system includes a processor configured to access projection images. The projection images comprise at least one feature of interest enhanced by a contrast agent. The processor is further configured to generate a contrast agent null image based on the projection images, generate a bone mask based on the contrast agent null image, and generate a bone extracted image based on the bone mask.

In accordance with an additional aspect of the present technique, an imaging system is provided. The imaging system includes a radiation source and a detector configured to acquire one or more projection images of an imaged volume. The one or more projection images comprise at least one feature of interest enhance by a contrast agent. The imaging system further includes a processor configured to access the one or more projection images, to generate a contrast agent null image from the one or more projection images, to generate a bone mask from the contrast agent null image, and to generate a bone extracted image based on the bone mask.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is generally related to extracting features of interest from radiographic images. Such feature extraction techniques may be useful in a variety of imaging contexts, such as medical imaging and non-medical imaging. Though the present discussion provides examples in a medical imaging context, those skilled in the art will appreciate that the application of these techniques in other contexts, such as for non-medical imaging is well within the scope of the present techniques. Moreover, though the present discussion provides examples with respect to projection images acquired via a dual energy CT system, the technique may be applied or extended to extract features of interest from projection images acquired via other imaging modalities such as general radiography systems, computed tomography (CT) systems, tomosynthesis systems, C-arm systems, and so forth.

Figure 1:
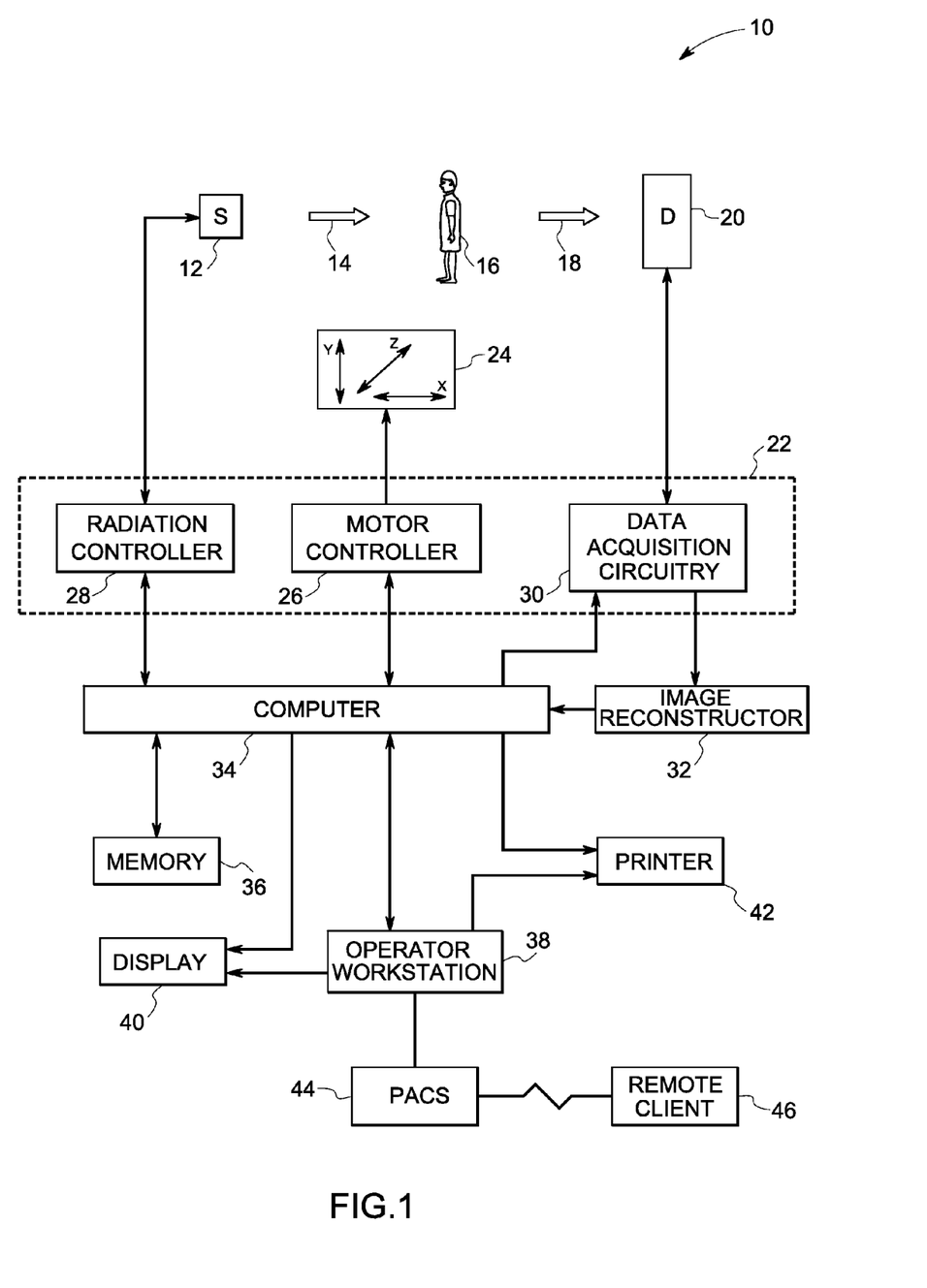
FIG. 1 depicts an exemplary imaging system for acquiring and analyzing image in accordance with one aspect of the present technique.

Referring now to FIG. 1, an imaging system 10 for use in accordance with aspects of the present technique is illustrated. The imaging system 10 is adapted to acquire projection images or sinograms and to process the acquired images for extracting features of interest in accordance with aspects of the present technique. In the illustrated embodiment, the imaging system 10 includes a radiation source 12, such as an X-ray source. A collimator (not shown) may be positioned adjacent to the radiation source 12. The collimator typically defines the size and shape of the stream of radiation 14 that passes into a region in which a subject, such as a human patient 16, is positioned. An unattenuated portion of the radiation 18 passes through the subject, which provides the attenuation, and impacts a detector array, represented generally by reference numeral 20. It should be noted that portions of the radiation 14 may extend beyond the boundary of the patient 16 and may impact detector 20 without being attenuated by the patient 16. In general, as discussed below, different tissues of the body will absorb or attenuate the radiation differently, allowing the production of image data that can be used to differentiate between such tissues.

The detector 20 is generally formed by a plurality of detector elements, which detect the radiation 18 that pass through or around the subject. For example, the detector 20 may include multiple rows and/or columns of detector elements arranged as an array. Each detector element, when impacted by an X-ray flux, produces an electrical signal that represents the integrated energy of the X-ray beam at the position of the element between subsequent signal readout of the detector 20. Typically, signals are acquired at one or more view angle positions around the subject of interest so that a plurality of radiographic views may be collected. These signals are acquired and processed to reconstruct an image of the features within the subject, as described below.

The radiation source 12 is controlled by a system controller 22, which furnishes power, control signals and so forth for imaging sequences. Moreover, the detector 20 is coupled to the system controller 22, which commands acquisition of the signals generated in the detector 20. The system controller 22 may also execute various signal processing and filtration functions, such as for initial adjustment of dynamic ranges, interleaving of digital image data, and so forth. In general, system controller 22 commands operation of the imaging system 10 to execute examination protocols and to process acquired data. In the present context, system controller 22 may also include signal processing circuitry, typically based upon a general purpose or application-specific digital computer, and associated memory circuitry. The associated memory circuitry may store programs and codes executed by the computer, configuration parameters, image data, and so forth. For example, the associated memory circuitry may store programs or codes for implementing the present technique.

In the embodiment illustrated in FIG. 1, system controller 22 may control the movement of a motion subsystem 24 via a motor controller 26. In the depicted imaging system 10, the motion subsystem 24 may move the source 12, the collimator, and/or the detector 20 in one or more directions in space with respect to the patient 16. It should be noted that the motion subsystem 24 might include a support structure, such as a gantry, C-arm or other movable support structure, on which the source 12 and/or the detector 20 may be disposed. The motion subsystem 24 may further enable the patient 16, or more specifically a patient table, to be displaced with respect to the source 12 and the detector 20 to generate images of particular areas of the patient 16.

As will be appreciated by those skilled in the art, the source 12 of radiation may be controlled by a radiation controller 28, which forms a part of the system controller 22. The radiation controller 28 may be configured to provide power and timing signals to the radiation source 12. Further, the system controller 22 may comprise a data acquisition circuitry 30. In this exemplary embodiment, the detector 20 is coupled to the system controller 22, and more particularly to the data acquisition circuitry 30. The data acquisition circuitry 30 receives data collected by readout electronics of the detector 20. In particular, the data acquisition circuitry 30 typically receives sampled analog signals from the detector 20 and converts the data to digital signals for subsequent processing by an image reconstructor 32 and/or a computer 34.

The computer 34 is typically coupled to the system controller 22. The data collected by the data acquisition circuitry 30 may be transmitted to the image reconstructor 32 and/or the computer 34 for subsequent processing and reconstruction. For example, the data collected from the detector 20 may undergo pre-processing and calibration at the data acquisition circuitry 30, the image reconstructor 32, and/or the computer 34 to condition the data to represent the line integrals of the attenuation coefficients of the scanned objects. The processed data may then be reordered, filtered, and backprojected to formulate an image of the scanned area. As will be appreciated by those skilled in the art, although the present techniques may be used with projection X-ray systems, when used with CT or tomosynthesis systems, in addition to typical filtered back-projection reconstruction algorithms, any suitable reconstruction algorithm may be employed, including statistical reconstruction approaches. Once reconstructed, the image produced by the imaging system 10 reveals an internal region of interest of the patient 16 which may be used for diagnosis, evaluation, and so forth.

The computer 34 may comprise or communicate with a memory 36 that can store data processed by the computer 34 or data to be processed by the computer 34. It should be understood that any type of computer accessible memory device capable of storing the desired amount of data and/or code may be utilized by such an exemplary system 10. Moreover, the memory 36 may comprise one or more memory devices, such as magnetic or optical devices, of similar or different types, which may be local and/or remote to the system 10. The memory 36 may store data, processing parameters, and/or computer programs comprising one or more routines for performing the processes described herein. Furthermore, memory 36 may be coupled directly to system controller 22 (not shown) to facilitate the storage of acquired data.

The computer 34 may also be adapted to control features enabled by the system controller 22, i.e., scanning operations and data acquisition. Furthermore, the computer 34 may be configured to receive commands and scanning parameters from an operator via an operator workstation 38 which may be equipped with a keyboard and/or other input devices. An operator may thereby control the system 10 via the operator workstation 38. Thus, the operator may observe the reconstructed image and other data relevant to the system from operator workstation 38, initiate imaging, and so forth.

A display 40 coupled to the operator workstation 38 may be utilized to observe the reconstructed image. Additionally, a printer 42 coupled to the operator workstation 38 may print the scanned image. The display 40 and the printer 42 may also be connected to the computer 34, either directly or via the operator workstation 38. Further, the operator workstation 38 may also be coupled to a picture archiving and communications system (PACS) 44. It should be noted that PACS 44 might be coupled to a remote system 46, such as a radiology department information system (RIS), hospital information system (HIS) or to an internal or external network, so that others at different locations may gain access to the image data.

It should be further noted that the computer 34 and operator workstation 38 may be coupled to other output devices that may include standard or special purpose computer monitors and associated processing circuitry. One or more operator workstations 38 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the internet, virtual private networks, and so forth.

Figure 2:
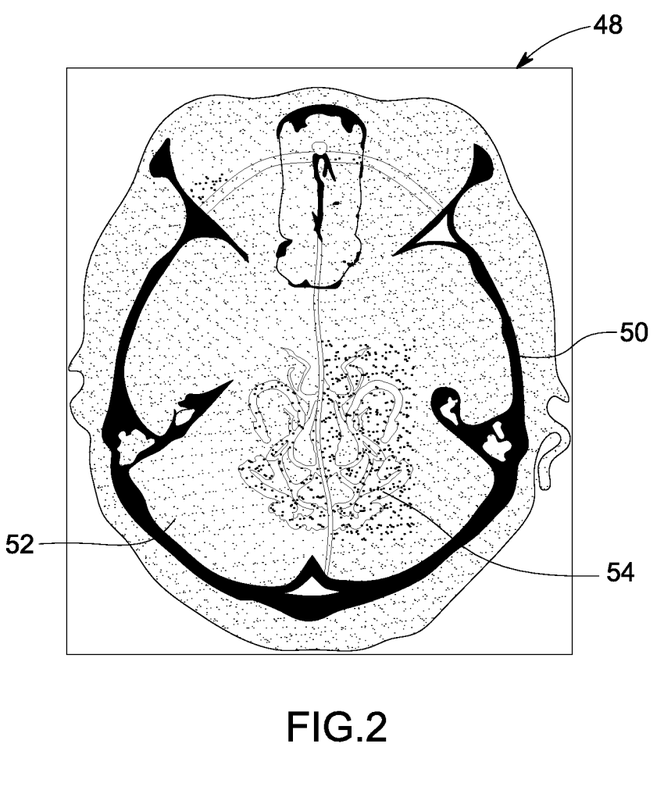
FIG. 2 depicts an anatomy with different structures imaged via the system of FIG. 1.

A wide variety of technique may be employed to analyze and/or evaluate the acquired projection images and/or the reconstructed images for diagnostic purposes. For example, the exemplary imaging system 10 may be adapted to acquire sets of projection images of the imaged object, generate a reconstructed image based on acquired projection images, and/or extract various features of interest from projection image or reconstructed image for detailed evaluation or examination. The features of interest may include bones, soft tissues, vasculature (blood vessel network), organs and so forth. Referring now to FIG. 2, an image representation 48 of an anatomy (e.g., brain) imaged by the system 10 of FIG. 1 is illustrated. The image representation may include different features such as bones 50, soft tissues 52 and/or blood vessels 54. As noted above, the blood vessel may be enhanced by use of a contrast agent.

The exemplary imaging system 10 or other such processor based image analysis system may acquire/access projection images and process the same to extract one or more features of interest by the techniques discussed herein. Additionally, the imaging system 10 or other such processor based image analysis system may process the projection images to reconstruct CT images. In particular, as will be appreciated by those of ordinary skill in the art, control logic and/or automated routines for performing the techniques and steps described herein may be implemented by the imaging system 10 of FIG. 1 or by any other processor based image analysis system, either by hardware, software, or combinations of hardware and software. For example, suitable code may be accessed and executed by the computer 34 to perform some or all of the techniques described herein. Similarly application specific integrated circuits (ASICs) configured to perform some or all of the techniques described herein may be included in the computer 34 and/or the system controller 22.

Figure 3:
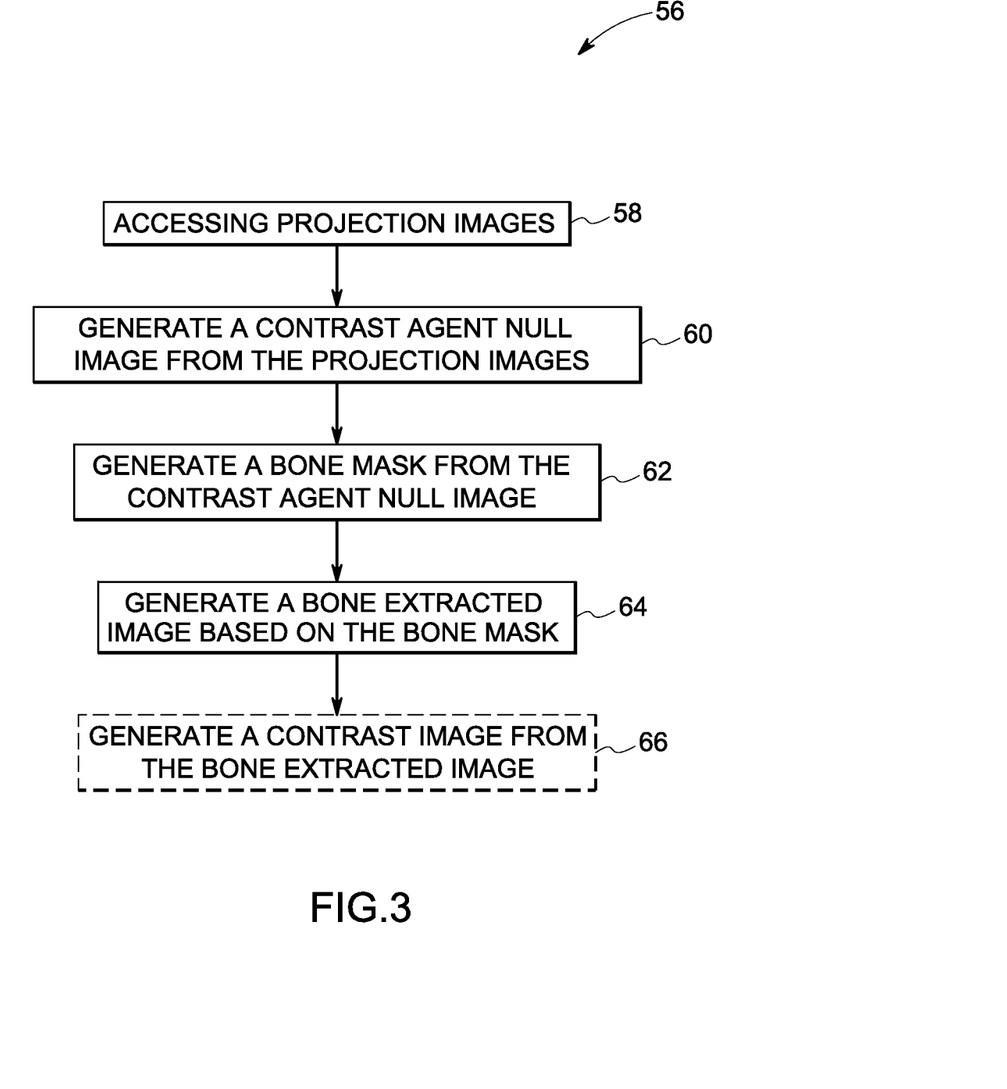
FIG. 3 is a flowchart illustrating an exemplary process for extracting one or more features of interest (e.g., different tissue types) from a contrast-enhanced radiographic image in accordance with aspects of the present technique.

For example, referring now to FIG. 3, exemplary control logic 56 for extracting one or more features of interest (e.g., different tissue types) from a contrast-enhanced radiographic image via a system such as imaging system 10 is depicted in accordance with aspects of the present technique. As illustrated in the flowchart, the control logic 56 includes the step of accessing one or more projection images at step 58. As will be appreciated by those skilled in the art, the one or more projection images may include at least one feature of interest enhanced by a contrast agent (e.g., iodine). The control logic 56 further includes the steps of generating a contrast agent null image from the one or more projection images at step 60, generating a bone mask from the contrast agent null image at step 62, and generating a bone extracted image based on the bone mask at step 64. Additionally, the control logic 56 may include the step of generating a contrast image from the bone extracted image at step 66.

Figure 4:
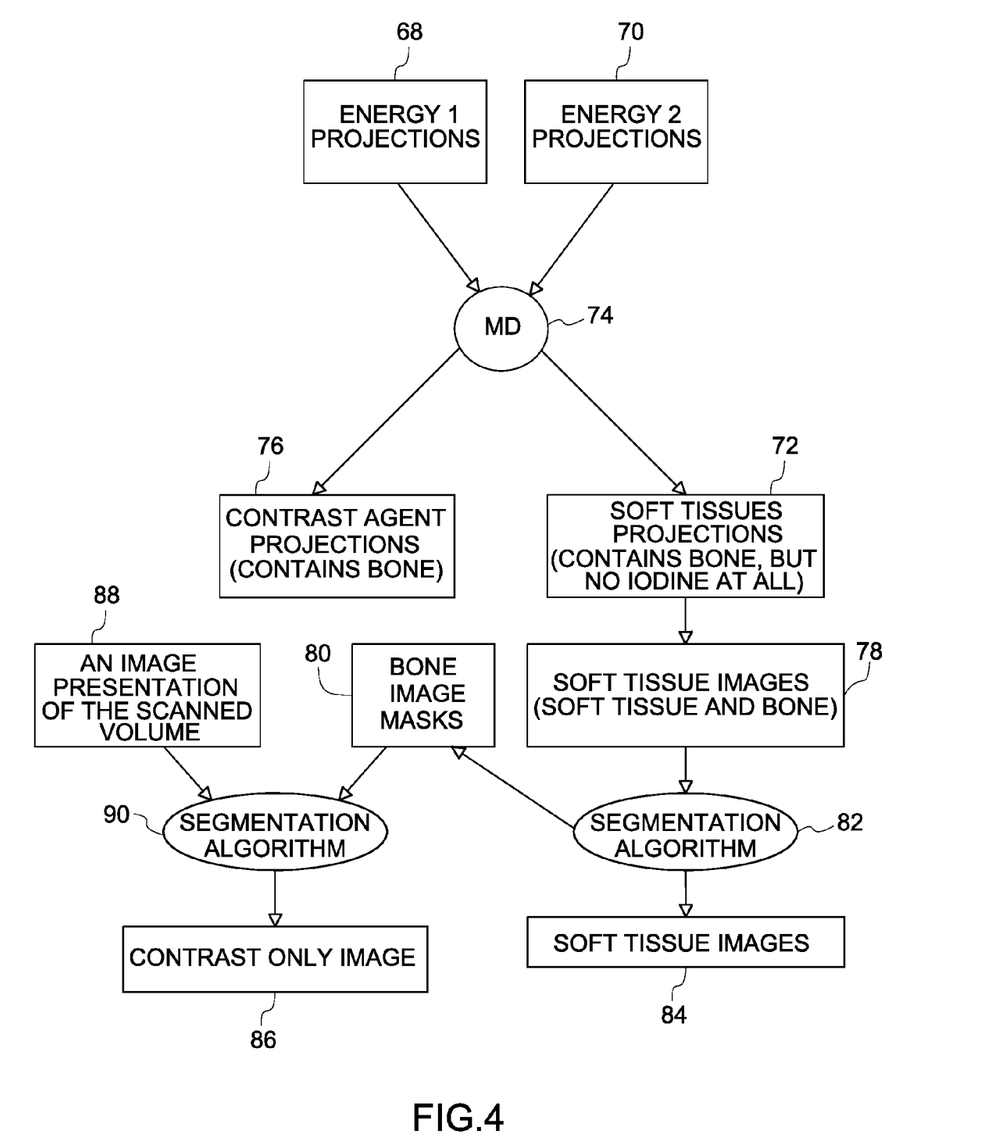
FIG. 4 is a flowchart illustrating the exemplary process of FIG. 3, in greater detail and in accordance with aspects of the present technique.

By means of further example, the feature extraction technique illustrated in FIG. 3 may further be elaborated as shown in FIG. 4. In the illustrated process set forth in FIG. 4, one or more projection images 68, 70 that represent the radiation attenuation measurements are accessed via a processor based image analysis system or acquired via an imaging system, such as system 10 of FIG. 1. As noted above, the projection images may be acquired by exposing an anatomy of interest to the imaging system 10 where the radiation source and the detector are configured to move with respect to each other. In the illustrated embodiment, the projection images 68 and 70 of the anatomy of interest are acquired by exposing the anatomy to two different X-ray energy levels respectively. As will be appreciated by those skilled in the art, such acquisition may be accomplished via a dual energy X-ray or CT system.

The acquired projection images 68 and 70 may include at least one feature of interest. In one embodiment, the feature of interest may be a blood vessel network or a vasculature. Alternatively, the feature of interest may include any specific tissue or an organ. Again, as noted above, the feature of interest may be enhanced via a use of contrast agent, such as iodine. As will be appreciated by those skilled in the art, the patient (anatomy of interest) may be administered with the contrast agent prior to and/or during the image acquisition.

A contrast agent null projection image 72 may then be generated from the projection images 68 and 70. In one embodiment, the contrast agent null image may be generated via a material decomposition technique 74. For example, in certain embodiments, a projection based material decomposition technique may be employed with soft tissue and contrast agent as the material bases. As will be appreciated by those skilled in the art, the material decomposition technique 74 removes the contrast agent with high accuracy, as the atomic number of the material in the contrast agent is known and is fixed for a given type of contrast agent. Thus, the material decomposition technique works incisively to remove the contrast agent, thereby leaving the projection image 72 with the absence of any contrast agent. As will be appreciated by those skilled in the art, in the absence of contrast agent, the bones can be segmented with greater accuracy. As noted above, the material decomposition technique 74 may also be applied to generate a contrast agent projection image (bone extracted projection image) 76. However, because the attenuation of the contrast agent may be close to certain tissues, such as bone, the generated projection image 76 will typically contain some bone for the reasons stated above.

As will be appreciated by those skilled in the art, the material decomposition technique involves converting the measured projections into a set of density line integral projections. The density line integral projection may then be reconstructed to form a density map or image of each respective basis material, such as bone, soft tissue, and/or contrast agent maps. Thus, the density maps or images maybe associated with volume rendering of the basis material, i.e., bone, soft tissue, and/or contrast agent, in the imaged volume.

The contrast agent null projection image 72 may then be reconstructed via the image reconstructor or the processor to generate a contrast agent null image 78. As will be appreciated by one skilled in the art, the reconstructed image 78 does not include the contrast agent enhanced feature (i.e., the feature of interest) as the contrast agent has been analytically removed or minimized in the contrast agent null projection images. Thus, in the illustrated embodiment, the image 78 contains soft tissues and bones but no vasculature (that is enhanced by the use of contrast agent). It should be noted that the image reconstructor and/or the processor may form a part of the image analysis system or the imaging system.

A bone mask 80 may then be generated from the image 78 by employing any image segmentation techniques 82. In one embodiment, any automated bone segmentation and extraction techniques may be applied to generate the bone mask 80. It should be noted that the generated bone mask 80 may be a binary mask of the bone. Additionally, it should be noted that, the image segmentation techniques 82 may also generate soft tissue image 84 in the process of generating bone mask 80.

The generated bone mask 80 may then be employed to generate a bone extracted image or a contrast only image 86. In one embodiment, the bone mask may be applied to an image representation of the imaged anatomy (anatomy of interest) 88 to generate the bone extracted image or the contrast only image 86. It should be noted that any image segmentation technique 90 may be used to generate the bone extracted image or the contrast only image 86 from the image representation of the anatomy of interest 88. Further, it should be noted that, the contrast only image 86 may be generated from the bone extracted image by employing any image segmentation techniques to separate the contrast agent enhanced feature of interest and the soft tissues.

As will be appreciated by those skilled in the art, the image representation 88 may be an original polychromatic beam image, a material decomposed image, a combined high/low kilovoltage peak (kVp) images, or a derived monochromatic image 74 of the anatomy of interest. For example, the images produced from polychromatic radiation beam are of high-peak power in geometry and is practically for imaging with much diagnostic accuracy the anatomy or the patient. The material decomposed images are the images processed using projection based material decomposition technique, in which the images represent the density of the basis materials. Further, it should be noted that monochromatic images are formed from the material decomposed images by linearly weighting the two material decomposed images. A combined high/low kVp image is generally formed by linearly weighting the high and low kVp images for the better signal to noise ratio. As will be appreciated by those skilled in the art, the high and low kVp images may be produced by altering the potential of the radiation source. As noted above, the bone mask may be applied to any of the above mentioned image representations to generate bone extracted image. For example, in one embodiment, a combined or a three-dimensional reconstructed image may be generated based upon the acquired projection images. The bone-extracted image may then be generated by applying the bone mask to the combined image. Alternatively, a monochromatic image may be generated based upon the acquired projection images and the bone-extracted image may be generated by applying the bone mask to the monochromatic image.

Figure 5:
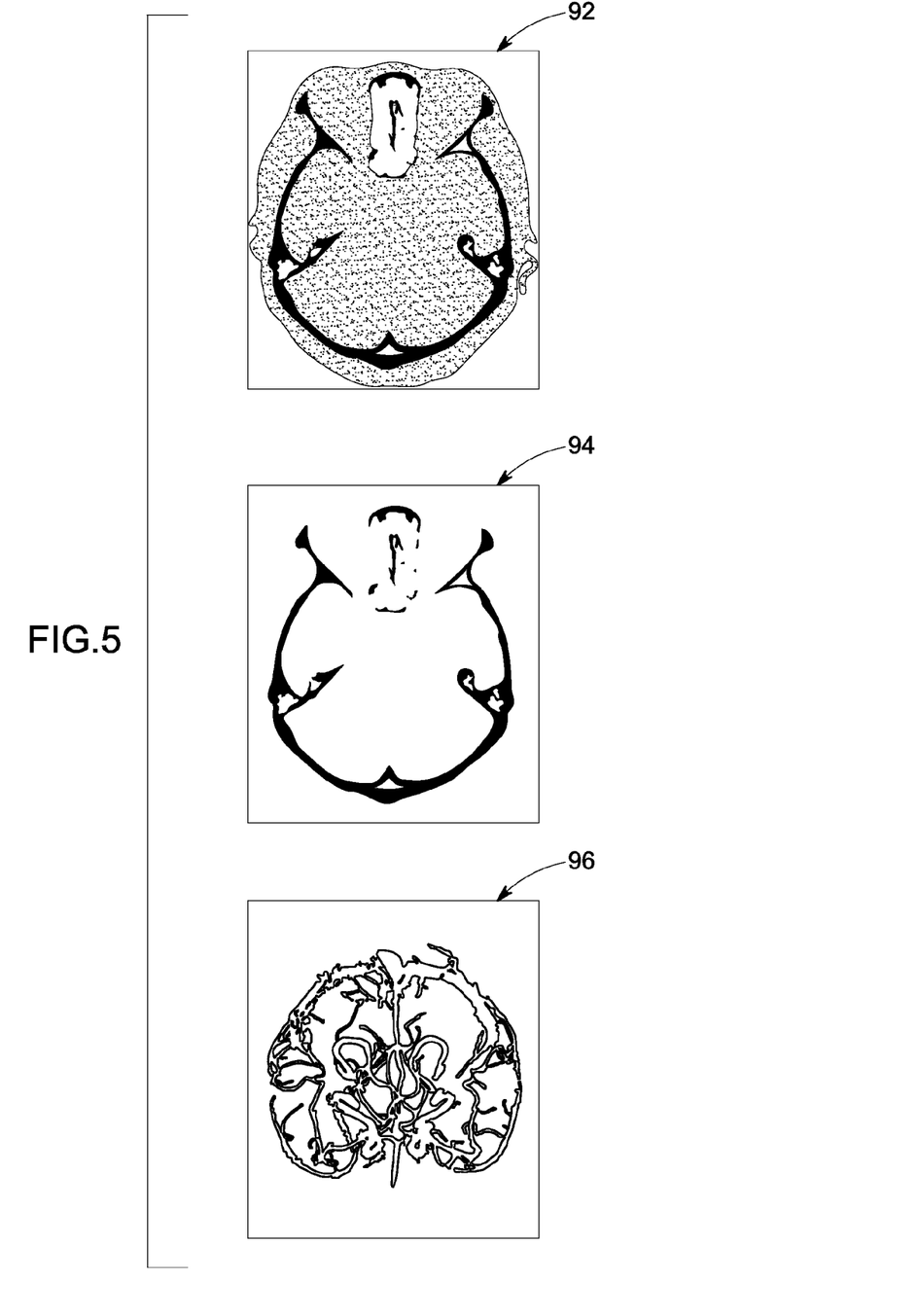
FIG. 5 depicts images of structures segmented from the image of FIG. 2 via the process of FIGS. 3 and 4.

FIG. 5 illustrates various images generated at different stages of feature extraction technique discussed above. As will be appreciated by those skilled in the art, the illustrated images (contrast agent null image 92, bone mask 94, and image of vasculature 96) depict one or more structures extracted from the projection images of the imaged anatomy via the process described in FIGS. 3 and 4 above. The contrast agent null image 92 is generated at step 60 of the control logic 56, the bone mask 94 is generated at step 62 of the control logic 56, and the image 96 of the contrast enhanced vasculature (i.e., the extracted feature of interest) is generated at step 64 or 66 of the control logic 56. It should be noted that soft tissue image (not shown) may also be generated by employing step 66 of the control logic 56. As noted above, the contrast agent null image 92 may be obtained through material decomposition techniques.

In short, the present technique provides a novel approach to automatically extract one or more features of interest from the projection images. In particular, the technique may be useful for automatically extracting the features that includes the different organs, bones, vasculature and so forth. According to the present technique, the two or more projection images are being acquired once the contrast agents are administered in the local anatomy of interest. The contrast agents cause attenuation of the X-ray beam as it passes through the vessels and organs and hence enhance those areas in the projection images. The basis material decomposition technique may be used in the process of generating a contrast agent null image. An image volume with the absence of contrast agent could be accomplished based on the knowledge of fixed chemical composition of the material in the contrast agent. The contrast null image can then be used to segment the bones more effectively. The segmentation process is then initiated or instructed to remove the masked bones to generate an accurate contrast only image. The contrast only image or bone extracted image could be obtained by applying the bone mask to an image representation of the anatomy of interest that may be a material decomposed image, an original polychromatic beam image, or a derived monochromatic image.

As will be appreciated by those skilled in the art, the techniques described in various embodiments discussed above provide improved images of the one or more feature of interest in a manner heretofore unobtainable, and in an automated fashion, thereby improving efficiency and accuracy. The accurate and reliable images of the features of interest may also improve the diagnostic capability of radiologists and/or physicians. Further, the accurate estimation of blood vessel parameters is a prerequisite for automated visualization and analysis of healthy or diseased blood vessels. Additionally, the techniques described in the various embodiments discussed above do not require the anatomy (and hence the subject) to be motionless for longer durations. This greatly increases the patient comfort and extends the applicability of the feature extraction technique to portions of the anatomy that are in motion (e.g., heart).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of extracting one or more features of interest from one or more projection images, the method comprising:
   accessing projection images comprising at least one feature of interest enhanced by a contrast agent;
   generating a contrast agent null image based on the projection images;
   generating a bone mask based on the contrast agent null image, wherein the bone mask only includes an image of bone; and
   generating a bone extracted image based on the bone mask.

2. The method of claim 1, wherein the projection images are obtained from a tomosynthesis system, a general radiographic X-ray system, an X-ray C-arm system, a computed tomography system, or a dual energy computed tomography system.

3. The method of claim 1, wherein the projection images are obtained by exposure of a subject to at least two different X-ray energy levels.

4. The method of claim 1, wherein the at least one feature of interest comprises a vasculature.

5. The method of claim 1, wherein generating the contrast agent null image comprises applying a material decomposition technique.

6. The method of claim 1, wherein generating the bone mask comprises applying an automated bone segmentation and extraction technique.

7. The method of claim 1, wherein the bone mask is a binary mask.

8. The method of claim 1, wherein the bone extracted image is obtained by applying the bone mask to a material decomposed image, an original polychromatic beam image, or a derived monochromatic image.

9. The method of claim 1, comprising generating a combined image based upon the projection images, wherein the bone-extracted image is generated by applying the bone mask to the combined image.

10. The method of claim 1, comprising generating a monochromatic image based upon projection images, and wherein the bone-extracted image is generated by applying the bone mask to the monochromatic image.

11. The method of claim 1, further comprising generating a contrast image based on the bone extracted image via image segmentation technique.

12. A method of extracting one or more features of interest from projection images, the method comprising:
   acquiring the projection images of an anatomy of interest by exposing the anatomy of interest to at least two different X-ray energy levels, the anatomy comprising at least one feature of interest administered with a contrast agent;
   generating a contrast agent null image based on the projection images via a material decomposition technique;
   generating a binary bone mask from the contrast agent null image via an automated bone segmentation technique, wherein the binary bone mask only includes an image of bone; and
   generating a bone extracted image by comparing an image representation of the anatomy of interest and the binary bone mask.

13. An image analysis system, comprising:
   a processor configured to access projection images, generate a contrast agent null image based on the projection images, generate a bone mask based on the contrast agent null image, wherein the bone mask only includes an image of bone, and generate a bone extracted image based on the bone mask, wherein the projection images comprise at least one feature of interest enhanced by a contrast agent.

14. The image analysis system of claim 13, wherein the processor is configured to generate the bone extracted image by applying the bone mask to a material decomposed image, an original polychromatic beam image, or a derived monochromatic image.

15. The image analysis system of claim 13, wherein the processor is further configured to generate a contrast image based on the bone extracted image via image segmentation technique.

16. An imaging system, comprising:
   a radiation source and a detector configured to acquire one or more projection images of an imaged volume, the one or more projection images comprising at least one feature of interest enhanced by a contrast agent; and
   a processor configured to access the one or more projection images, to generate a contrast agent null image from the one or more projection images, to generate a bone mask from the contrast agent null image, wherein the bone mask only includes an image of bone, and to generate a bone extracted image based on the bone mask.

17. The imaging system of claim 16, wherein the processor is configured to reconstruct an image of the imaged volume based on the one or more projection images.

18. The imaging system of claim 16, wherein the processor is configured to generate the bone extracted image by applying bone mask to an image representation of the imaged volume.

19. The imaging system of claim 16, wherein the processor is further configured to generate a contrast image based on the bone extracted image via image segmentation technique.

20. A tangible, non-transitory computer readable media, comprising:
   code adapted to access one or more projection images, the one or more projection images comprising at least one feature of interest enhance by a contrast agent;
   code adapted to generate a contrast agent null image based on the one or more projection images;
   code adapted to generate a bone mask based on the contrast agent null image, wherein the bone mask only includes an image of bone; and
   code adapted to generate a bone extracted image based on the bone mask.

21. The computer readable media of claim 20, wherein code adapted to generate the bone extracted image comprises code adapted to apply bone mask to an image representation of an imaged anatomy.

22. The computer readable media of claim 20, further comprising code adapted to generate a contrast image based on the bone extracted image via image segmentation technique.

* * * * *